United States Patent
De Coulon et al.

(10) Patent No.: US 8,161,795 B2
(45) Date of Patent: Apr. 24, 2012

(54) THERMAL GAS SENSOR

(75) Inventors: Yves De Coulon, Saint-Blaise (CH); Olivier Chetelat, Hauterive (CH); Marc Brodard, Rolle (CH); Emmanuel Onillon, Les Hauts-Geneveys (CH)

(73) Assignee: Neroxis SA, Neuchatel (CH)

( * ) Notice: Subject to any disclaimer, the term of this patent is extended or adjusted under 35 U.S.C. 154(b) by 437 days.

(21) Appl. No.: 12/527,523

(22) PCT Filed: Feb. 8, 2008

(86) PCT No.: PCT/EP2008/051571
§ 371 (c)(1),
(2), (4) Date: Aug. 17, 2009

(87) PCT Pub. No.: WO2008/101822
PCT Pub. Date: Aug. 28, 2008

(65) Prior Publication Data
US 2010/0116024 A1    May 13, 2010

(30) Foreign Application Priority Data
Feb. 15, 2007   (CH) .......................... 257/07

(51) Int. Cl.
*G01N 25/18*   (2006.01)
(52) U.S. Cl. ........................ 73/25.03; 73/23.2
(58) Field of Classification Search ........... 73/23.2, 73/25.03
See application file for complete search history.

(56) References Cited

U.S. PATENT DOCUMENTS

| | | | |
|---|---|---|---|
| 4,887,280 A | 12/1989 | Reisenfeld | |
| 5,345,213 A * | 9/1994 | Semancik et al. | 338/34 |
| 5,515,714 A | 5/1996 | Sultan et al. | |
| 5,777,206 A | 7/1998 | Zuchner et al. | |
| 6,838,287 B2 | 1/2005 | Bonne et al. | |
| 7,231,807 B2 | 6/2007 | Ingrisch et al. | |

(Continued)

FOREIGN PATENT DOCUMENTS

DE    10 2004 047 786    4/2006

(Continued)

OTHER PUBLICATIONS

Pascal Tardy et al., "Dynamic thermal conductivity senor for gas detection", Sensors and Actuators B, Elsevier Sequioa S.A., Lausanne, CH, vol. 98, No. 1, Mar. 1, 2004, XP004493655, ISSN: 0925-4005, pp. 63-68.

(Continued)

*Primary Examiner* — Hezron E Williams
*Assistant Examiner* — Rodney T Frank
(74) *Attorney, Agent, or Firm* — Young & Thompson

(57) ABSTRACT

A physical gas sensor of thermal type capable of determining the concentrations of a gas mixture even in the presence of humidity by measuring the thermal diffusivity and conductivity includes a cell with thermal conductivity whose frequency response to the gases is known, in particular in respect of humidity, delivering a signal Vm representative of the concentration of the gas. This cell is excited by a pulsed signal so that a processing can be carried out at different analysis frequencies: at low frequency and at higher frequency. The output signals from the two processing chains are combined in the circuit (60) so as to provide the levels of concentration of the gas and the concentration of the water vapour. The signals obtained may also be re-combined together with components of the signal Vm of various passbands.

13 Claims, 2 Drawing Sheets

U.S. PATENT DOCUMENTS 7,286,925 B2 10/2007 Lang

FOREIGN PATENT DOCUMENTS

| EP | 0 254 906 | 2/1988 |
| EP | 0 439 950 | 8/1991 |
| WO | 97/02486 | 1/1997 |
| WO | 99/34201 | 7/1999 |
| WO | 00/54841 | 9/2000 |
| WO | 01/13101 | 2/2001 |
| WO | 2004/051245 | 6/2004 |

OTHER PUBLICATIONS

International Search Report dated May 23, 2008, from corresponding PCT application.

Swiss Search Report from corresponding Swiss application.

* cited by examiner

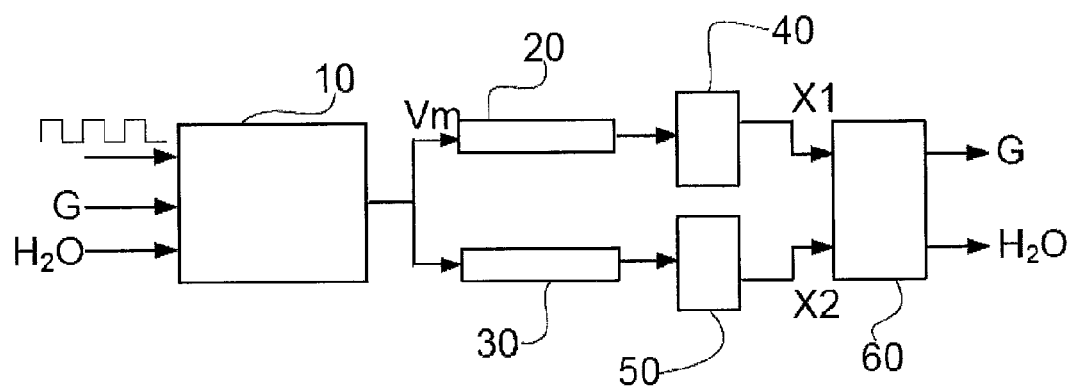
Fig. 3
Fig. 4.a
Fig. 4.b
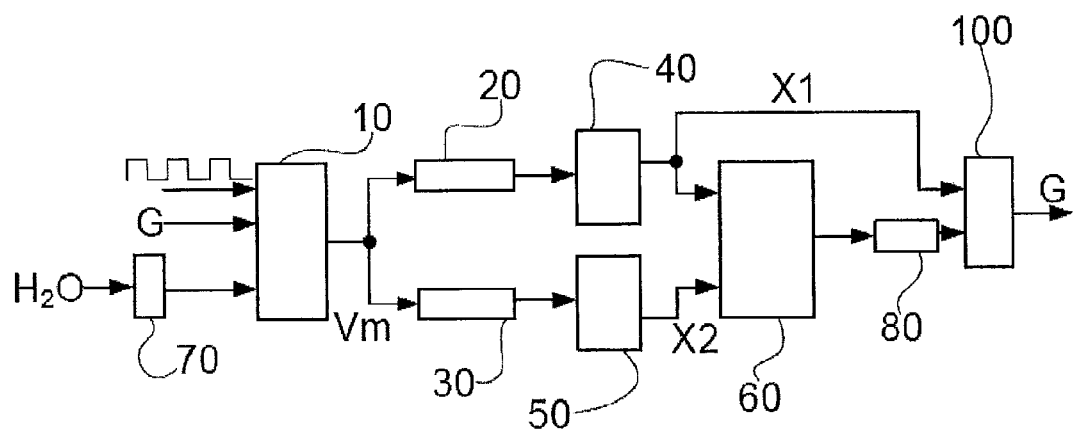
Fig. 5

THERMAL GAS SENSOR

TECHNICAL FIELD

The present invention relates to a gas sensor and more particularly to an integrated physical gas sensor of the thermal type, and capable of accurately measuring the concentration of a gas mixture even in the presence of humidity and without the latter perturbing the measurement.

STATE OF THE ART

A physical gas thermal conductivity sensor, marketed under the code of MGSM 2201 by the Swiss firm Silsens SA, is based on the measurement of thermal conductivity, between a hot point and a cold point, of a gas or a gas mixture. Indeed, the thermal conductivity of a gas or a gas mixture notably varies with its chemical nature. A sensor of this type allows gases such as $CO_2$, $H_2$ and $CH_4$ to be detected in the presence of air, and provides the advantage of having low consumption combined with large long-term stability. This gas sensor with thermal conductivity is made in a silicon substrate and requires thin film deposition techniques as well as micro-structuration techniques. The sensor conventionally comprises an integrated heating element positioned on a membrane, which is electrically and thermally insulating. Two thin film resistors are used, one for the miniature heating element of low thermal inertia and the other one for a sensor for measuring temperature at the membrane around which flow the gases for which determination of the concentration is sought. A direct current (about 5 mA) provides the heating function. Moreover, two similar reference resistors, structured in the same thin metal film, are also integrated in proximity to the membrane in order to provide compensation of the changes in room temperature. The sensor is arranged on the silicon substrate so that a gas flow may occur around the membrane. The temperature of the measurement resistor depends on the gas which surrounds it, so that a change in the composition of the gas causes variations in the temperature behavior of this same resistor. However, in order to take into account possible changes in humidity of the gases to be measured, it was hitherto necessary to affix a humidity sensor, such as the one marketed under the code HS1101 by the French corporation Humirel, to the gas sensor described earlier. It is easily understood that the requirement of incorporating such a humidity sensor has a penalizing effect on the cost, the bulkiness and the complexity of the global system.

Other solutions for measuring the concentration of gases have already been proposed, such as for example the solution described in U.S. Pat. No. 6,838,287 or even the use of a gas filter requiring silica gel (or Silicagel) or active coal. The solution of the US patent does not solve the problem of humidity and the gas filter does not lend itself to miniaturization.

DISCLOSURE OF THE INVENTION

An object of the present invention is to provide an improved sensor for detecting a gas mixture by thermal conductivity and diffusivity, capable of finding a remedy to the drawbacks mentioned above. More particularly, an object of the invention is to provide an improved method of use and of implementation of an integrated thermal conductivity sensor which results in a gas concentration measurement less sensitive to the presence of $H_2O$ molecules.

In order to determine, and subsequently compensate the presence of humidity in the gas mixture, it was suggested that measurements be conducted in several frequency ranges benefiting from the fact that the frequency response of the sensor in the system varies in a known way depending on the concentration, on the nature of the gas(es) and on the humidity present. Thus, for a measurement of a binary gas mixture and of humidity for example, the sensor will operate at a low frequency and at a higher frequency and the frequency response of the sensor will be examined for different gases. Such a solution, which combines an AC and DC current control of the heating resistor, an analysis of the frequency response and knowledge of the reaction time of the sensor towards gases, has the purpose of measuring several gas parameters, such as their thermal conductivity and their thermal diffusivity, with which, by adding new equations to the measurement system, it is possible to get rid of the influence of humidity without having to resort to a humidity sensor.

Thus, more particularly, the invention relates to a sensor, for determining the concentration of at least one gas (G) in a humid gas mixture, including a thermal conductivity measurement cell to which the gas mixture is submitted, said cell comprising:

a membrane of low thermal inertia on which a heating resistor and a measurement resistor are positioned and delivering a signal (Vm) provided by said measurement resistor, and a circuit for determining said concentration.

According to the invention, the heating resistor is powered by a current including an alternating component, the determination circuit comprises a first low frequency processing chain for the provided signal (Vm) and at least one second chain (30, 50) for processing the signal (Vm) at a higher frequency than that of the first chain. Further, the output signals (X1, X2) of the first and second chains are combined in order to extract the concentration of the gas (G) and that of humidity.

The first processing chain may comprise a first band-pass filter and a second computation circuit for demodulating the output signal from the band-pass filter.

The second processing chain may also comprise a second band-pass filter and a second computation circuit for demodulating the output signal of the second band-pass filter.

Advantageously, the first and second computation circuits compute the sum of the squares of the samples of the output signals of the first and second band-pass filters.

The combination of the output signals of the first and second chains is a linear combination which may be expressed as follows:

$$\text{Conc. }(G) = a_{11}.X1 + a_{12}.X2, \text{ and}$$

$$\text{Conc. }(H_2O) = a_{21}.X1 + a_{22}.X2,$$

wherein Conc. (G) and Conc. ($H_2O$) designate the concentrations of the gas to be measured G and of steam, respectively.

The gas mixture which may be sent into the measurement cell is first filtered so that its water content only varies slowly over time.

The sensor may further include an averaging circuit for determining the steam concentration.

The invention also relates to a method for determining the concentration of at least one gas (G) in a humid gas mixture, applying a measurement cell as described above to which the gas mixture is submitted. The method according to the invention includes the following steps:

obtaining a first output signal (X1) provided by a first low frequency processing chain for said provided signal (Vm), obtaining a second output signal (X2) provided by a second processing chain for said signal (Vm) at a higher frequency that that of the first chain, combining the first and second output signals (X1, X2) in order to extract the concentration of said at least one gas (G) and that of humidity.

BRIEF DESCRIPTION OF THE DRAWINGS

Other objects, characteristics and advantages of the present invention will become apparent upon reading the following description of particular exemplary embodiments; said description being made with reference with the appended drawings wherein:

FIG. 3 shows a first alternative of a sensor according to the present invention;

FIG. 4 shows examples of excitation signals which may be applied to the sensor of the invention; and FIG. 5 shows an improved alternative of the sensor of FIG. 3.

EMBODIMENT(S) OF THE INVENTION

Figure 1:
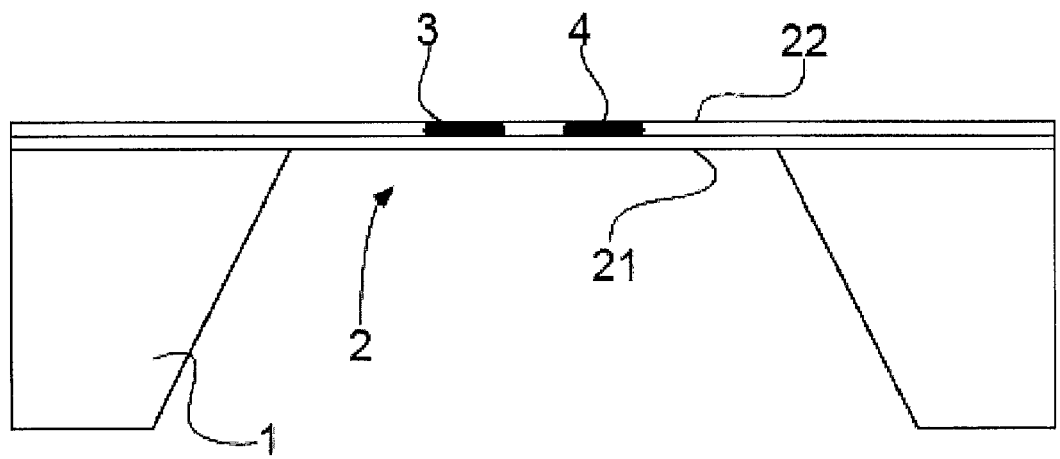
FIG. 1 is a sectional view of a measurement cell of a gas sensor which may be used within the scope of the present invention.

FIG. 1 shows a measurement cell which includes a membrane 2 for example made on a silicon substrate 1 by using conventional photolithographic techniques. The membrane 2 includes a silicon nitride layer 21 which makes up the lower portion of the membrane 2. Thin layers defining two resistors 3 and 4 were deposited on the layer 21. The latter are positioned in proximity to each other and may be in platinum, nickel or an alloy of both of these materials. After depositing the resistors 3 and 4, a silicon oxide protective layer 22 may be deposited on the layer 21. As a non-limiting example, the membrane has a surface of 1 mm$^2$ and the layers 21 and 22 each have a thickness of 300 nm. As indicated hereafter, the resistor 3 is used as a heating resistor while the resistor 4 is used as a resistor for measuring the temperature of the membrane. The flow of gases, the concentration of which is intended to be measured, is directed onto the membrane, above and below the latter.

Figure 2:
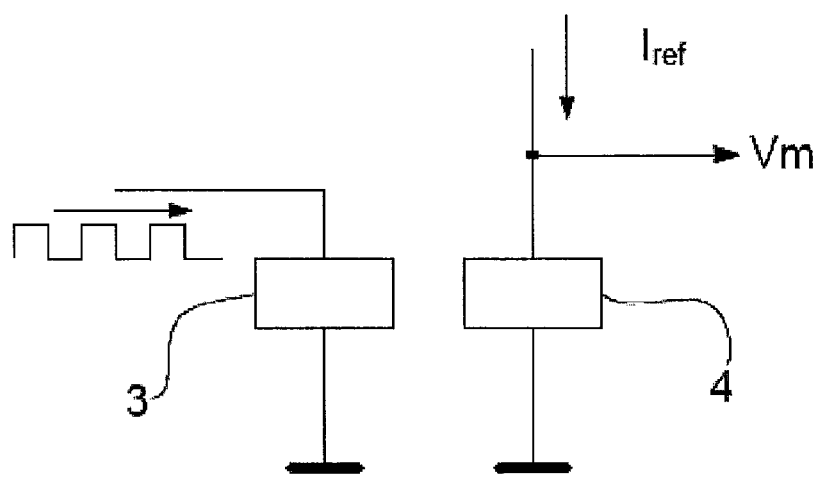
FIG. 2 shows an electric block diagram of the cell of FIG. 1.

With the diagram of FIG. 2, the operating principle of the cell of FIG. 1 may be explained. The heating resistor 3, for example with a value of 200Ω, is powered for example by a pulsed signal at a frequency of 1 Hz and with an amplitude of the order of 0.5 Volt. The measurement resistor 4 receives a current Iref of a few μA, and develops on its terminals a voltage Vm=Iref.RM, RM being the value of the resistor 4. This value is influenced by the temperature of the heating resistor located nearby on the one hand and by the chemical composition of the gas mixture flowing around the measurement resistor on the other hand. Thus, the voltage Vm is the input variable of the circuit associated with the measurement cell for determining the concentration of the gases according to the present invention.

A first alternative sensor according to the invention is illustrated in FIG. 3. This sensor comprises a measurement cell 10, for example of the type described in connection with FIG. 1, a filtering circuit 20 of the band-pass type receiving the signal Vm provided by the measurement cell, a first circuit 40 for computing the power of the signal provided by the circuit 20 and delivering a signal X1, a filtering circuit 30 of the band-pass type also receiving the signal Vm, a second circuit 50 for computing the power of the signal provided by the circuit 30 and delivering a signal X2 and a computation circuit 60 which from signals X1 and X2, provides the concentration values of the gases found in the measurement cell.

In the relevant example, the gas mixture comprises in addition to air, a gas G and humidity ($H_2O$). A signal pulsed at a frequency of 1 Hz is applied to the cell 10 in order to power the heating resistor of the latter. The voltage signal Vm generated by the cell is representative, as mentioned earlier, of the thermal and mass properties of the composition of the gas mixture, such as thermal diffusivity, thermal conductivity, specific heat and gas density. This signal is then filtered by the first band-pass filter 20 on the one hand, and by the second band-pass filter 30 on the other hand. The first band-pass filter 20 is a filter, for example of the first order, the bandwidth of which is comprised between 0 and a maximum frequency which depends on the bandwidth of the measurement cell, for example 15 Hz. The output signal of the filter 20 is applied to the computation circuit 40 which computes the power of this signal. To do this the output signal of the filter 20 is for example sampled and the circuit 40 performs summation of the squares of these samples over a given period, for example one second. The filter 30 typically has a bandwidth comprised between 15 Hz (maximum frequency of the band-pass filter 20) and 60 Hz. The circuit 50 performs the same operation on the output signal of the filter 30 as the circuit 40 on the output signal of the filter 20. The circuits 40 and 50 perform computation of power, which is equivalent to a computation of an envelope, or more generally to a demodulation of the input signal. The filter 20 and the circuit 40 form a first processing chain, a so-called low frequency chain, while the filter 30 and the circuit 50 form a second processing chain at a higher frequency. The output signals X1 and X2 of the circuits 40 and 50 are then applied to the computation circuit 60, which solves the following equation:

Conc. $(G)=a_{11}.X1+a_{12}.X2$, and

Conc. $(H_2O)=a_{21}.X1+a_{22}.X2$, wherein Conc. (G) and Conc. ($H_2O$) designate the concentrations of the gas to be measured G and of steam in the gas mixture, respectively. The coefficients $a_{11}$, $a_{12}$, $a_{21}$, and $a_{22}$ are determined during calibration of the sensor with gas mixtures of known composition and concentration. The equations given above correspond for the concentrations of the gases, to linear functions of the input variables X1 and X2; it is obvious that it is not possible to be limited to such functions and that other more complex functions of these same variables may also be used.

FIG. 4 shows examples of excitation signals which may be applied to the heating resistor of the measurement cell. In FIG. 4.a, a simple pulsed signal for which the frequency is 1 Hz is illustrated. In FIG. 4.b, the same signal is illustrated on which a high frequency 15 Hz signal has been superposed. Superposition of the high frequency signal (from 15-20 Hz) on the base signal illustrated in FIG. 4.a has the purpose of enhancing the high frequency signal and improving the signal-to-noise ratio of the latter.

FIG. 5 shows an improved alternative of the sensor of FIG. 3, the equivalent elements in both figures bearing the same references. Indeed, with the alternative of FIG. 3, the accuracy of the concentration measurements may in certain applications prove to be insufficient, notably when the humidity rate varies during the measurement. The result is that the measurement of the sought concentration of the gas has a too high noise percentage. In order to get rid of this problem, the use of humidity filter for example based on silica gel or active coal at the input of the measurement cell 10 is suggested on the one hand, and the filtration of the noise on the output signal by for example carrying out averaging of the latter, on the other hand.

The humidity filter 70 has the function of preventing the humidity rate in the measurement cell from varying too rapidly, it therefore operates like a known low pass-filter. As an example, it will be selected in such a way that the relative change in the humidity rate in the cell remains below 5% over a period of half an hour.

The output signal of the computation circuit 60, which represents the estimated value of the water concentration, is applied to a low-pass filter 100. This filter should for better efficiency, have frequency characteristics similar to those of the filter 70. The output of the filter 100 is applied to a second computation circuit 100 which receives on a second input the output signal X1 of the circuit 40. The circuit 100 delivers the value of the concentration of the gas G by solving the following equation:

$$\text{Conc. }(G)=a_{11}-(a_{12}.a_{21})/a_{22}.X1+(a_{12}/a_{22}).f(H_2O),$$

wherein the function f() represents the transfer function of the filter 80 and $H_2O$ is the value of the estimated concentration of humidity provided by the circuit 60.

In the description above, the mixture of a gas in air with humidity was considered. Of course, it is possible to apply the principles of the invention for measuring the concentration of several gases mixed with air and steam. In this case, the number of frequency ranges in the measurement circuit will be increased as many times as necessary for having as many equations as there are unknowns to be determined.

It is obvious that all the operations described above with conventional terminology may be performed in the digital domain by means of a processor advantageously placed on the measurement cell.

A particularly interesting application of the invention is the measurement of carbon dioxide ($CO_2$) in humid air, such as measurement being able to be made in order to provide an alarm in the case of a too high concentration value. Other applications aim at measuring hydrogen, methane, notably in connection with fuel cells, biogas, the main advantage as indicated earlier, being the possibility of accurately determining the concentration of a gas at least in a humid atmosphere without however requiring any humidity sensor.

This method may be extended to a polynomial and non-linear combination of characteristics which may be extracted from the measurement signal such as the rise time, the amplitude, the average value . . . It may also be applied to any ternary or quasi-ternary mixture of gases where the third gas to be measured would replace humidity.

The invention claimed is:

1. A sensor for determining the concentration of at least one gas (G) in a humid gas mixture, including a thermal conductivity measurement cell to which the gas mixture is submitted, said cell comprising
   a membrane of low thermal inertia on which a heating resistor and a measurement resistor are positioned and delivering a signal (Vm) provided by said measurement resistor, said heating resistor is powered by a current including an alternating component, and
   a circuit for determining said concentration, wherein said determination circuit comprises a first frequency processing chain for said provided signal (Vm) and at least one second processing chain for said signal (Vm) at a higher frequency than that of the first chain, and in that the output signals (X1, X2) of said first and second chains are combined in order to extract the concentration of said at least one gas (G) and that of humidity.

2. The sensor of claim 1, wherein said first processing chain comprises a first band-pass filter and a first computation circuit for demodulating the output signal of said band-pass filter.

3. The sensor of claim 1, wherein said second processing chain comprises a second band-pass filter and a second computation circuit for demodulating the output signal of said band-pass filter.

4. The sensor of claims 2, wherein said second processing chain comprises a second band-pass filter and a second computation circuit for demodulating the output signal of said band-pass filter, and said first and second computation circuits compute the sum of the squares of the samples of the output signals of the band-pass and band-pass filters, respectively.

5. The sensor of claim 1, wherein the combination of said output signals of said first and second chains is a linear combination.

6. The sensor of claim 5, wherein said linear combination is expressed as follows:

$$\text{Conc. }(G)=a_{11}.X1+a_{12}.X2, \text{ and}$$

$$\text{Conc. }(H_2O)=a_{21}.X1+a_{22}.X2,$$

wherein Conc. (G) and Conc. ($H_2O$) designate the concentrations of the gas to be measured G and of steam, respectively.

7. The sensor of claim 1, wherein the gas mixture sent into the measurement cell is first filtered so that its water content only varies slowly over time.

8. The sensor according to claim 5, said sensor further including an averaging circuit for determining the steam concentration.

9. The sensor of claim 1, wherein the combination of said output signals of said first and second chains is a polynomial combination.

10. A method for determining the concentration of at least one gas (G) in a humid gas mixture, applying a thermal conductivity measurement cell to which the gas mixture is submitted, said cell comprising:
    a membrane on which a heating resistor and a measurement resistor are positioned and delivering a signal provided by said measurement resistor (Vm), said heating resistor being powered by a current including an alternating component, and
    a circuit for determining said at least one concentration,
said method including the following steps:
    obtaining a first output signal (X1) provided by a first frequency processing chain for said provided signal (Vm),
    obtaining a second output signal (X2) provided by a second processing chain for said signal (Vm) at a higher frequency than that of the first chain,
    combining first and second output signals (X1, X2) in order to extract the concentration of said at least one gas (G) and that of humidity.

11. The method of claim 10, wherein the combination of said output signals of said first and second chains is a linear combination.

12. The method of claim 11, wherein said linear combination is expressed as follows:

$$\text{Conc. }(G)=a_{11}.X1+a_{12}.X2, \text{ and}$$

$$\text{Conc. }(H_2O)=a_{21}.X1+a_{22}.X2,$$

wherein Conc. (G) and Conc. ($H_2O$) designate the concentrations of the gas to be measured G and of steam, respectively.

13. The method of claim 10, wherein the combination of said output signals of said first and second chains is a polynomial combination.

* * * * *